US012561781B2

(12) United States Patent
Lewis et al.

(10) Patent No.: US 12,561,781 B2
(45) Date of Patent: Feb. 24, 2026

(54) METHODS, SYSTEMS, AND COMPUTER PROGRAM PRODUCT FOR VALIDATING DRUG PRODUCT PACKAGE CONTENT USING TIERED EVALUATION FACTORS

(71) Applicant: PARATA SYSTEMS, LLC, Durham, NC (US)

(72) Inventors: Russell F. Lewis, Dallas, TX (US); Arthur F. Swanson, Cary, NC (US); Todd Martin Jenkins, Raleigh, NC (US)

(73) Assignee: PARATA SYSTEMS, LLC, Durham, NC (US)

( * ) Notice: Subject to any disclaimer, the term of this patent is extended or adjusted under 35 U.S.C. 154(b) by 549 days.

(21) Appl. No.: 17/932,861

(22) Filed: Sep. 16, 2022

(65) Prior Publication Data

US 2023/0098966 A1     Mar. 30, 2023

Related U.S. Application Data

(60) Provisional application No. 63/249,304, filed on Sep. 28, 2021.

(51) Int. Cl.
   *G06T 7/00*          (2017.01)
   *G06T 11/00*         (2006.01)
   (Continued)

(52) U.S. Cl.
   CPC ............ *G06T 7/0004* (2013.01); *G06T 11/00* (2013.01); *G06V 10/776* (2022.01); *G16H 20/10* (2018.01);
   (Continued)

(58) Field of Classification Search
   CPC .... G06V 20/62; G06V 10/82; G06V 2201/09; G06T 5/70; G06T 2207/20084;
   (Continued)

(56) References Cited

U.S. PATENT DOCUMENTS 8,374,965 B2 *   2/2013   Friend et al. ........... G06F 21/00
                                                        705/50
9,233,767 B2 *   1/2016   Amano et al. .......... B65B 5/103
                          (Continued)

FOREIGN PATENT DOCUMENTS

CN         107256426 A     10/2017
KR         101943217 B1    1/2019
                (Continued)

OTHER PUBLICATIONS

International Preliminary Report on Patentability corresponding to PCT/US2022/077073; dated Apr. 11, 2024, (6 pages).
                (Continued)

*Primary Examiner* — Matthew C Bella
*Assistant Examiner* — Daniel Joseph Santos
(74) *Attorney, Agent, or Firm* — Myers Bigel, P.A.

(57)          ABSTRACT

A method includes receiving a drug product package containing one or more drug products therein; evaluating the one or more drug products contained in the drug product package based on a plurality of drug product evaluation factors, the plurality of drug product evaluation factors including an enhanced scrutiny factor; assigning a validation score to the drug product package based on evaluating the one or more drug products contained in the drug product package, a magnitude of the validation score being greater with decreasing patient risk; and validating the drug product package. Validating the drug product package comprises: validating the drug product package based on a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold; or identifying the
                (Continued)

drug product package as requiring manual validation responsive to the presence of the enhanced scrutiny factor.

20 Claims, 8 Drawing Sheets

(51) Int. Cl.
*G06V 10/776* (2022.01)
*G16H 20/10* (2018.01)
*G16H 50/30* (2018.01)

(52) U.S. Cl.
CPC ... *G16H 50/30* (2018.01); *G06T 2207/30108* (2013.01)

(58) Field of Classification Search
CPC .... G06T 5/60; G06T 5/77; G06T 5/92; G06T 7/0004; G06T 7/11; G06T 7/136; G06T 7/194; G06T 2207/20081; G16H 70/40; G16H 20/10; G16H 50/70; G16H 50/30; G16H 10/60; G16H 20/13; G16H 50/20; G16H 10/20; G06Q 10/087; G06Q 40/08; G06Q 50/22; G06Q 10/06; G06F 19/3456; G06F 19/328; G06F 19/3431; G06N 20/00
USPC .......................................................... 382/103
See application file for complete search history.

(56) References Cited

U.S. PATENT DOCUMENTS

| | | | | | |
|---|---|---|---|---|---|
| 10,492,987 | B2 * | 12/2019 | Blalock et al. | ........... | A61J 1/00 |
| 11,065,180 | B2 * | 7/2021 | Grosfils et al. | ......... | A61J 1/035 |
| 11,120,913 | B2 * | 9/2021 | Dey et al. | .............. | G16H 50/30 |
| 2006/0015536 | A1 * | 1/2006 | Buchanan et al. | ...... | G06F 12/00 |
| | | | | | 707/200 |
| 2009/0030722 | A1 | 1/2009 | Wiener et al. | | |
| 2010/0145506 | A1 | 6/2010 | Waugh et al. | | |
| 2012/0065999 | A1 * | 3/2012 | Takatoku et al. | ...... | G06Q 50/22 |
| | | | | | 705/3 |
| 2012/0330684 | A1 | 12/2012 | Jacobs et al. | | |
| 2015/0178674 | A1 | 6/2015 | Yonaha et al. | | |
| 2015/0363570 | A1 * | 12/2015 | Hanina et al. | ...... | G06F 19/3456 |
| 2020/0143946 | A1 * | 5/2020 | Russell | .................. | G16H 50/30 |
| 2020/0156397 | A1 * | 5/2020 | Luciano | .................. | B42D 1/00 |
| 2020/0279630 | A1 | 9/2020 | Gersten | | |
| 2021/0201434 | A1 * | 7/2021 | Natali et al. | ............. | G06K 9/00 |
| | | | | | 382/128 |
| 2021/0330684 | A1 * | 10/2021 | Dudley et al. | ........... | G06K 9/18 |
| | | | | | 705/3 |
| 2025/0143972 | A1 | 5/2025 | Yuyama | | |

FOREIGN PATENT DOCUMENTS

| | | |
|---|---|---|
| WO | 0006078 A2 | 2/2000 |
| WO | 2022165135 A1 | 8/2022 |
| WO | 2022177954 A1 | 8/2022 |

OTHER PUBLICATIONS

Extended European Search Report corresponding to EP 22877494.9, Feb. 3, 2025, 11 pp.

International Search Report and Written Opinion corresponding to PCT/US2022/077073; dated Jan. 17, 2023 (9 pages).

* cited by examiner

100

| Packaging System Interface 135 | 120 |  150 |

PMS 110

140

Data Sources 165

130a          • • •          130b

Package Validation Engine 160

155

METHODS, SYSTEMS, AND COMPUTER PROGRAM PRODUCT FOR VALIDATING DRUG PRODUCT PACKAGE CONTENT USING TIERED EVALUATION FACTORS

RELATED APPLICATION

The present application claims priority from and the benefit of U.S. Provisional Application No. 63/249,304, filed Sep. 28, 2021, the disclosure of which is hereby incorporated herein by reference in its entirety.

BACKGROUND

The present disclosure relates generally to the packaging of drug products, and, in particular, to methods, systems, and computer program products for validating content of drug product packages.

Drug product packaging systems may be used in facilities, such as pharmacies, hospitals, long term care facilities, and the like to dispense medications to fill prescriptions. These drug product packaging systems may include systems designed to package medications in various container types including, but not limited to, pouches, vials, bottles, blister-card, and strip packaging. Strip packaging is a type of packaging wherein medications are packaged in individual pouches for administration on a specific date and, in some cases, at a specific time. Typically, individual pouches are removably joined together and often provided in rolls. The pouches can be separated from the roll when needed.

Once a drug product package is generated, it may go through an automated validation process to ensure that the contents match the packaging order. Such validation may ensure that a customer gets the proper medication both in terms of medication type and quantity and may reduce the risk of packaging medications together that may have harmful interactions.

SUMMARY

In some embodiments of the inventive concept, a method comprises: receiving a drug product package containing one or more drug products therein; evaluating the one or more drug products contained in the drug product package based on a plurality of drug product evaluation factors, the plurality of drug product evaluation factors including an enhanced scrutiny factor; assigning a validation score to the drug product package based on evaluating the one or more drug products contained in the drug product package, a magnitude of the validation score being greater with decreasing patient risk; and validating the drug product package. Validating the drug product package comprises: validating the drug product package based on a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold; or identifying the drug product package as requiring manual validation responsive to the presence of the enhanced scrutiny factor.

In still other embodiments, the drug product package is part of a fulfillment of a packaging order. The method further comprises: defining the enhanced scrutiny factor for the packaging order In other embodiments, the drug product package is part of a fulfillment of a packaging order. The method further comprises: defining the first threshold and the second threshold for the packaging order.

In still other embodiments, the plurality of drug product evaluation factors include a plurality of enhanced scrutiny factors, the plurality of enhanced scrutiny factors comprising a first subset of enhanced scrutiny factors and a second subset of enhanced scrutiny factors.

In still other embodiments, validating the drug product package comprises: validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors; and validating the drug product package based on a second comparison of the magnitude of the validation score with a second threshold responsive to an absence of any of the plurality of enhanced scrutiny factors.

In still other embodiments, validating the drug product package further comprises: identifying the drug product package as requiring manual validation responsive to the presence of the at least one enhanced scrutiny factor of the second subset of enhanced scrutiny factors.

In still other embodiments, the plurality of enhanced scrutiny factors comprises one or more of: an age of a patient to whom the one or more drug products is prescribed; a gender of the patient to whom the one or more drug products is prescribed; a pharmacogenomic profile of the patient to whom the one or more drug products is prescribed; a financial cost of the one or more of the drug products; an interaction between the one or more of the drug products; a side effect of the one or more of the drug products; a propensity of the one or more of the drug products to create debris in the drug product package; packaging order history information for the patient to whom the one or more drug products is prescribed; recall information for the one or more drug products; a potential for exceeding a safe dosing for the one or more of the drug products; and/or an indication that the one or more of the drug products includes a substituted drug product that differs from a packaging order.

In still other embodiments, validating the drug product package comprises validating the drug product package using an artificial intelligence engine.

In still other embodiments, validating the drug product package using the artificial intelligence engine comprises: detecting, using the artificial intelligence engine, the one or more drug products contained in the drug product package.

In still other embodiments, detecting, using the artificial intelligence engine, the one or more drug products contained in the drug product package comprises: generating, using the artificial intelligence engine, a modified image of the drug product package that has selected content removed from a surface thereof.

In still other embodiments, detecting, using the artificial intelligence engine, the one or more drug products contained in the drug product package comprises: detecting, using the artificial intelligence engine, characteristics of an image of the drug product package that are associated with a drug product packaging system; and generating, using the artificial intelligence engine, a modified image of the drug product package based on characteristics of the drug product packaging system.

In some embodiments of the inventive concept, a system comprises a processor; and a memory coupled to the processor and comprising computer readable program code embodied in the memory that is executable by the processor to perform operations comprising: receiving a drug product package containing one or more drug products therein; evaluating the one or more drug products contained in the drug product package based on a plurality of drug product evaluation factors, the plurality of drug product evaluation factors including an enhanced scrutiny factor; assigning a validation score to the drug product package based on evaluating the one or more drug products contained in the drug product package, a magnitude of the validation score being greater with decreasing patient risk; and validating the drug product package. Validating the drug product package comprises: validating the drug product package based on a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold; or identifying the drug product package as requiring manual validation responsive to the presence of the enhanced scrutiny factor.

In further embodiments, the plurality of drug product evaluation factors include a plurality of enhanced scrutiny factors, the plurality of enhanced scrutiny factors comprising a first subset of enhanced scrutiny factors and a second subset of enhanced scrutiny factors.

In still further embodiments, validating the drug product package comprises: validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors; and validating the drug product package based on a second comparison of the magnitude of the validation score with a second threshold responsive to an absence of any of the plurality of enhanced scrutiny factors.

In still further embodiments, validating the drug product package further comprises: identifying the drug product package as requiring manual validation responsive to the presence of the at least one enhanced scrutiny factor of the second subset of enhanced scrutiny factors.

In still further embodiments, the plurality of enhanced scrutiny factors comprises one or more of: an age of a patient to whom the one or more drug products is prescribed; a gender of the patient to whom the one or more drug products is prescribed; a pharmacogenomic profile of the patient to whom the one or more drug products is prescribed; a financial cost of the one or more of the drug products; an interaction between the one or more of the drug products; a side effect of the one or more of the drug products; a propensity of the one or more of the drug products to create debris in the drug product package; packaging order history information for the patient to whom the one or more drug products is prescribed; recall information for the one or more drug products; a potential for exceeding a safe dosing for the one or more of the drug products; and/or an indication that the one or more of the drug products includes a substituted drug product that differs from a packaging order.

In still further embodiments, validating the drug product package comprises validating the drug product package using an artificial intelligence engine.

In some embodiments of the inventive concept, a computer program product comprises a non-transitory computer readable storage medium comprising computer readable program code embodied in the medium that is executable by a processor to perform operations comprising: receiving a drug product package containing one or more drug products therein; evaluating the one or more drug products contained in the drug product package based on a plurality of drug product evaluation factors, the plurality of drug product evaluation factors including an enhanced scrutiny factor; assigning a validation score to the drug product package based on evaluating the one or more drug products contained in the drug product package, a magnitude of the validation score being greater with decreasing patient risk; and validating the drug product package. Validating the drug product package comprises: validating the drug product package based on a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold; or identifying the drug product package as requiring manual validation responsive to the presence of the enhanced scrutiny factor.

In other embodiments, the plurality of drug product evaluation factors include a plurality of enhanced scrutiny factors, the plurality of enhanced scrutiny factors comprising a first subset of enhanced scrutiny factors and a second subset of enhanced scrutiny factors.

In still other embodiments, validating the drug product package comprises: validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors; and validating the drug product package based on a second comparison of the magnitude of the validation score with a second threshold responsive to an absence of any of the plurality of enhanced scrutiny factors; and identifying the drug product package as requiring manual validation responsive to the presence of the at least one enhanced scrutiny factor of the second subset of enhanced scrutiny factors.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
FIG. 1 is a block diagram that illustrates a communication network including a drug product package validation system for validating a drug product package using tiered evaluation factors in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "data processing facility" includes, but it is not limited to, a hardware element, firmware component, and/or software component. A data processing system may be configured with one or more data processing facilities.

The term "drug product packaging system," as used herein, refers to any type of pharmaceutical dispensing system including, but not limited to, automated systems that fill vials, bottles, containers, pouches, blistercards, or the like with drug product, semi-automated systems that fill vials, bottles, containers, pouches, blistercards, or the like with drug product, and any combination of automated and semi-automated systems for filling a drug product package with drug product. Drug product packaging system also includes packaging systems for pharmaceutical alternatives, such as nutraceuticals and/or bioceuticals.

The terms "pharmaceutical" and "medication," as used herein, are interchangeable and refer to medicaments prescribed to patients either human or animal. A pharmaceutical or medication may be embodied in a variety of ways including, but not limited to, pill form capsule form, tablet form, and the like.

The term "drug product" refers to any type of medicament that can be packaged within a vial, bottle, container, pouch, blistercard, or the like by automated and semi-automated drug product packaging systems including, but not limited to, pills, capsules, tablets, caplets, gel caps, lozenges, and the like. Drug product also refers to pharmaceutical alternatives, such as nutraceuticals and/or bioceuticals. Example drug product packaging systems including management techniques for fulfilling packaging orders are described in U.S. Pat. No. 10,492,987 the disclosure of which is hereby incorporated herein by reference.

The term "drug product package" refers to any type of object that can hold a drug product including, but not limited to, a vial, bottle, container, pouch, blistercard, or the like.

Embodiments of the inventive concept are described herein in the context of a drug product package validation engine that includes one or more machine learning engines and artificial intelligence (AI) engines. It will be understood that embodiments of the inventive concept are not limited to particular implementations of the drug product package validation engine and various types of AI systems may be used including, but not limited to, a multi-layer neural network, a deep learning system, a natural language processing system, and/or computer vision system Moreover, it will be understood that the multi-layer neural network is a multi-layer artificial neural network comprising artificial neurons or nodes and does not include a biological neural network comprising real biological neurons. Embodiments of the inventive concept may be implemented using multiple AI systems or may be implemented by combining various functionalities into fewer or a single AI system.

Some embodiments of the inventive concept stem from a realization that drug product package validation systems, which are used to validate the contents of a drug product package to ensure that it is consistent with a packaging order and to ensure that the drug products contained therein may not be harmful to a recipient, use evaluation factors that are typically fixed and weighted equally. Embodiments of the inventive concept may provide a drug product package validation system that uses tiered evaluation factors where some of the evaluation factors are weighted as being more important than others. For example, the factors used in evaluating a drug product package during the validation process may include one or more enhanced scrutiny factors. The presence of one or more of these enhanced scrutiny factors may result in the drug product package being identified as requiring manual validation. In other embodiments, the presence of one or more of these enhanced scrutiny factors may result in the drug product package requiring the achievement of a higher validation score magnitude to be validated, where the validation score magnitude increases with decreasing patient risk, than would be required if the enhanced scrutiny factors were not present. The enhanced scrutiny factors may include, but are not limited to, an age of a patient to whom the one or more drug products is prescribed (some drug products are not approved for pediatric patients, geriatric patients, etc.); a gender a patient to whom the one or more drug products is prescribed (some drugs are not prescribed for all genders); a pharmacogenomic profile of a patient to whom the one or more drug products is prescribed (a patient's genetic profile may impact drug efficacy); a financial cost of the one or more of the drug products; an interaction between the one or more of the drug products (interaction information between drug products may be obtained, for example, with reference to commercially available drug product databases, such as First Data Bank and/or Medispan); a side effect of the one or more of the drug products; a propensity of the one or more of the drug products to create debris in the drug product package; a potential for exceeding a safe dosing for the one or more of the drug products; packaging order history information for the patient to whom the one or more drug products is prescribed (e.g., a patient should not take drug A if the patient has been prescribed drug B in the last six months or a patient should only take drug A if the patient has completed a regimen of drug 250 mg of drug B daily for the last three months); recall information for the one or more drug products; and/or an indication that the one or more of the drug products includes a substituted drug product that differs from a packaging order. In some embodiments, the evaluation factors used in the validation process, including any factors that are to be treated as enhanced scrutiny factors, may be defined or assigned through a management system operated by, for example, a pharmacist, hospital, medical center, or other entity responsible for packaging the drug product. The set of evaluation factors used during the validation process may, therefore, be specific to one or more specific drug product packaging orders or may be used generally over all drug product packaging orders. In some embodiment of the inventive concept, a further evaluation of the data associated with a packaging order may be done even before the packaging is performed. For example, an AI analysis of a patient's current and historical packaging orders may be performed to predict whether the current order may be incorrect, have inconsistencies or the like. For example, a new drug product that a patient has never been prescribed before may be included on a current packaging order. This may cause the packaging order to receive additional scrutiny either before or after packaging. As another example, a patient may routinely be prescribed a drug product package for a particular drug product every three months, but a current order for the patient does not include that drug product even though the patient is due for a refill. This may trigger additional review of the drug product packaging order before and/or after the drug product package is generated.

Referring to FIG. 1, a communication network 100 including a drug product package validation system, in accordance with some embodiments of the inventive concept, comprises a pharmacy management system (PMS) or host system 110, a packaging system server 120, a validation system server 155, and one or more drug product packaging systems 130*a* and 130*b* that are coupled via a network 140 as shown.

The PMS system 110 may be configured to manage and fill prescriptions for customers. As used herein, PMS systems may be used in pharmacies or may be used generally as batch-generating systems for other applications, such as dispensing nutraceuticals or bioceuticals. The PMS system 110 may be associated with a variety of types of facilities, such as pharmacies, hospitals, long term care facilities, and the like. The PMS system or host system 110 may be any system capable of sending a valid prescription to the one or more product packaging systems 130*a* and 130*b*. The packaging system server 120 may include a packaging system interface module 135 and may be configured to manage the operation of the drug product packaging systems 130*a* and 130*b*. For example, the packaging system server 120 may be configured to receive packaging orders from the PMS system 110 and to identify which of the drug product packaging systems 130*a* and 130*b* should be used to package particular individual orders or batches of orders. In addition, the packaging system server 120 may be configured to manage the operations of the drug product packaging systems 130*a* and 130*b*. For example, the packaging system server 120 may be configured to manage the inventory of drug product available through each of the drug product packaging systems 130*a* and 130*b*, to manage the drug product dispensing canisters assigned or registered to one or more of the drug product packaging systems 130*a* and 130*b*, to manage the operational status generally of the drug product packaging systems 130*a* and 130*b*, and/or to manage reports regarding the status (e.g., assignment, completion, etc.) of packaging orders, drug product inventory, order billing, and the like. A user 150, such as a pharmacist or pharmacy technician, may communicate with the packaging system server 120 using any suitable computing device via a wired and/or wireless connection. Although the user 150 is shown communicating with the packaging system server 120 via a direct connection in FIG. 1, it will be understood that the user 150 may communicate with the packaging system server 120 via one or more network connections. The user 150 may interact with the packaging system server 120 to approve or override various recommendations made by the packaging system server 120 in operating the drug product packaging systems 130*a* and 130*b*. The user 150 may also communicate with the PMS 110 as prescription orders may be entered manually into the PMS 110. The user 150 may also initiate the running of various reports as described above for the drug product packaging systems 130*a* and 130*b*. Although only two drug product packaging systems 130*a* and 130*b* are shown in FIG. 1, it will be understood that more than two drug product packaging systems or a single drug product packaging system may be managed by the packaging system server 120.

The drug product package validation system may include the validation system server 155, which includes a package validation engine(s) module 160 to facilitate validation of the contents of a drug product package through use of tiered evaluation factors. The validation system server 155 and package validation engine(s) module 160 may include a rules-based system for processing images of drug product packages and applying one or more evaluation factors from a set of tiered evaluation factors to generate a score for a drug product package. The score may then be compared with one or more validation score thresholds to validate the drug product package and/or identify the drug product package as requiring manual validation. In some embodiments, the validation system server 155 may include one or more AI systems to generate modified images of drug product packages with labeling content removed from one or more surfaces thereof, to detect in a drug product package image individual ones of one or more drug products contained in the drug product package, and/or to identify these drug products that have been detected in the drug product package image. In accordance with various embodiments of the inventive concept, the labeling content can be removed from any surface on the drug product package including multiple surfaces of the drug product package, such as the top, bottom, and sides of vials, front and back surfaces of pouches and blister packs, and the like. The one or more AI systems may also be configured to generate modified images of drug product packages to account for differences in packaging systems. Such AI systems are described, for example, in PCT International Publication Nos. WO 2022/177954 and WO 2022/165135 the disclosures of which are hereby incorporated herein by reference. The validation system server 155 may access data sources 165 as part of the drug product package validation process. These data sources 165 may include drug product reference sources, such as databases containing National Drug Codes (NDCs) or Drug Identification Numbers (DINs). The data sources 165 may also include packaging data from historical orders, which may be used in debris evaluation and may include drug product price information for identifying high-cost drug products in a package. The data sources 165 may further include characteristic information for drug products, such as capsules, pills, and the like, including size, shape, color, markings, or other identifying information.

It will be understood that the division of functionality described herein between the packaging system server 120/packaging system interface module 135 and the validation system server 155/package validation engine(s) module 160 is an example. Various functionality and capabilities can be moved between the packaging system server 120/packaging system interface module 135 and the validation system server 155/package validation engine(s) module 160 in accordance with different embodiments of the inventive concept. Moreover, in some embodiments, the packaging system server 120/packaging system interface module 135 and the validation system server 155/package validation engine(s) module 160 may be merged as a single logical and/or physical entity.

A network 140 couples the drug product packaging systems 130*a* and 130*b*, the PMS system 110, the packaging system server 120, and the validation system server 155 to one another. The network 140 may be a global network, such as the Internet or other publicly accessible network. Various elements of the network 140 may be interconnected by a wide area network, a local area network, an Intranet, and/or other private network, which may not be accessible by the general public. Thus, the communication network 140 may represent a combination of public and private networks or a virtual private network (VPN). The network 140 may be a wireless network, a wireline network, or may be a combination of both wireless and wireline networks.

The drug product package validation service using tiered drug product package evaluation factors service provided through the validation system server 155, and package validation engine(s) module 160, in some embodiments, may be implemented as a cloud service. In some embodiments, the drug product package validation service may be implemented as a Representational State Transfer Web Service (RESTful Web service).

Although FIG. 1 illustrates an example communication network that includes a drug product package validation system for validating a drug product package using tiered evaluation factors, it will be understood that embodiments of the inventive subject matter are not limited to such configurations, but are intended to encompass any configuration capable of carrying out the operations described herein.

Figure 2:
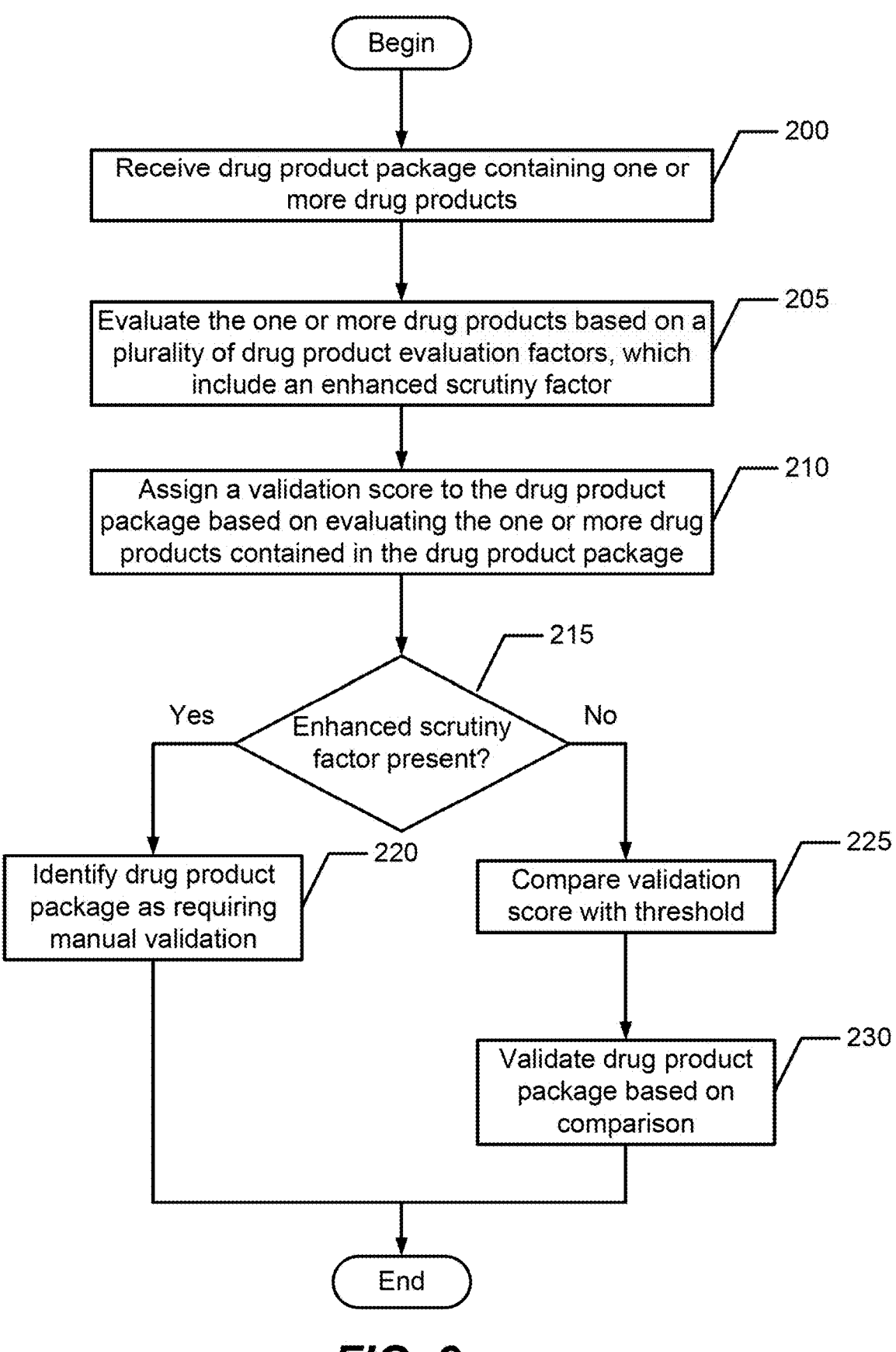
FIG. 2 is a flowchart that illustrates operations for validating a drug product package using tiered evaluation factors in accordance with some embodiments of the inventive concept.

FIG. 2 is a flowchart that illustrates operations for validating a drug product package using tiered evaluation factors in accordance with some embodiments of the inventive concept. Referring now to FIG. 2, operations begin at block 200 where a drug product package is received containing one or more drug products. The one or more drug products are evaluated based on a plurality of drug product evaluation factors, which include one or more enhanced scrutiny factors at block 205. In accordance with various embodiments of the inventive concept, the enhanced scrutiny factors may include, but are not limited to, an age of a patient to whom the one or more drug products is prescribed (some drug products are not approved for pediatric patients, geriatric patients, etc.); a gender of a patient to whom the one or more drug products is prescribed (some drugs are not prescribed for all genders); a pharmacogenomic profile of a patient to whom the one or more drug products is prescribed (a patient's genetic profile may impact drug efficacy); financial cost of the one or more of the drug products; an interaction between the one or more of the drug products (interaction information between drug products may be obtained, for example, with reference to commercially available drug product databases, such as First Data Bank and/or Medispan); a side effect of the one or more of the drug products; a propensity of the one or more of the drug products to create debris in the drug product package; a potential for exceeding a safe dosing for the one or more of the drug products; packaging order history information for the patient to whom the one or more drug products is prescribed (e.g., a patient should not take drug A if the patient has been prescribed drug B in the last six months or a patient should only take drug A if the patient has completed a regimen of drug 250 mg of drug B daily for the last three months); recall information for the one or more drug products; and/or an indication that the one or more of the drug products includes a substituted drug product that differs from a packaging order. The evaluation factors used in evaluating the one or more drug products contained in a drug product package, including any factors that are to be treated as enhanced scrutiny factors, may be defined or assigned through a management system operated by, for example, a pharmacy, hospital, medical center, or other entity responsible for packaging the drug product. In accordance with embodiments of the inventive concept, the evaluation factors used during the validation process may be specific to one or more specific drug product packaging orders or may be used generally over all drug product packaging orders. A validation score is assigned to the drug product package at block 210 based on the evaluation of the one or more drug products contained in the drug product package using the evaluation factors. A magnitude of the validation score increases with decreasing risk to the patient and/or the packaging entity.

Figure 3:
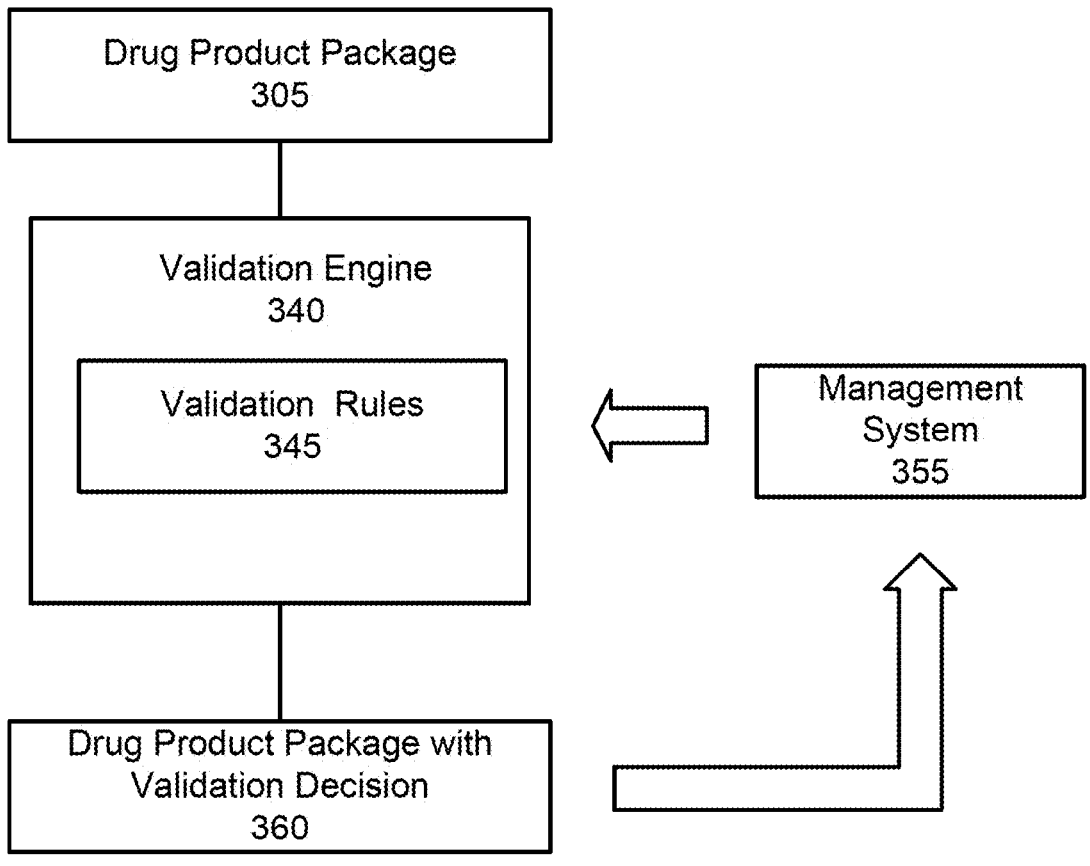
FIG. 3 is a block diagram that illustrates the drug product package validation system in accordance with some embodiments of the inventive concept.

FIG. 3 is a block diagram that illustrates a drug product validation system in accordance with some embodiments of the inventive concept. Referring to FIG. 3, a drug product package 305 is provided to the validation engine 340. The validation engine 340 is configured with validation rules 345 that may be provided via a management system 355 operated by a packaging entity, such as a pharmacy, medical center, or the like. These validation rules may define the drug product evaluation factors used in evaluating the drug product package including assigning or defining one or more of the drug product evaluation factors as being an enhanced scrutiny factor. The validation rules 345 may also include a methodology for generating a validation score for a drug product package along with one or more validation score thresholds and comparison logic for determining whether to validate a drug product package, identify the drug product package as requiring manual review, and/or invalidate a drug product package. The drug product package with an associated validation decision 360 may be output from the drug product validation system and the management system 355 may receive notice of the validation decision for the drug product package.

Returning to FIG. 2, operations continue at block 215 where an evaluation is made whether one or more of the enhanced scrutiny factors has been found to be present in evaluating the drug product package. In some embodiments, if one or more of the enhanced scrutiny factors are found to be present, then the drug product package is identified as requiring manual validation at block 220. If none of the enhanced scrutiny factors are found to be present, then the operations continue at block 225 where a magnitude of the validation score is compared with a threshold. For example, if the magnitude of the validation score exceeds the threshold, then the drug product package may be validated at block 230. If a drug product package goes to manual validation at block 220 and fails, various types of remediation approaches may be used in accordance with different embodiments of the inventive concept. For example, for drug product packaged in a strip, then the whole strip may not be rejected just one or more of the packages. In some embodiments, a message may be generated informing operators or pharmacists how to return drug product to inventory if possible. In some embodiments, it may be most cost efficient to discard low cost pills, packets, batches, and the like. For higher value drug products, however, the drug product package may be routed to a correction station where the package is opened and the drug product is replaced.

Figure 4:
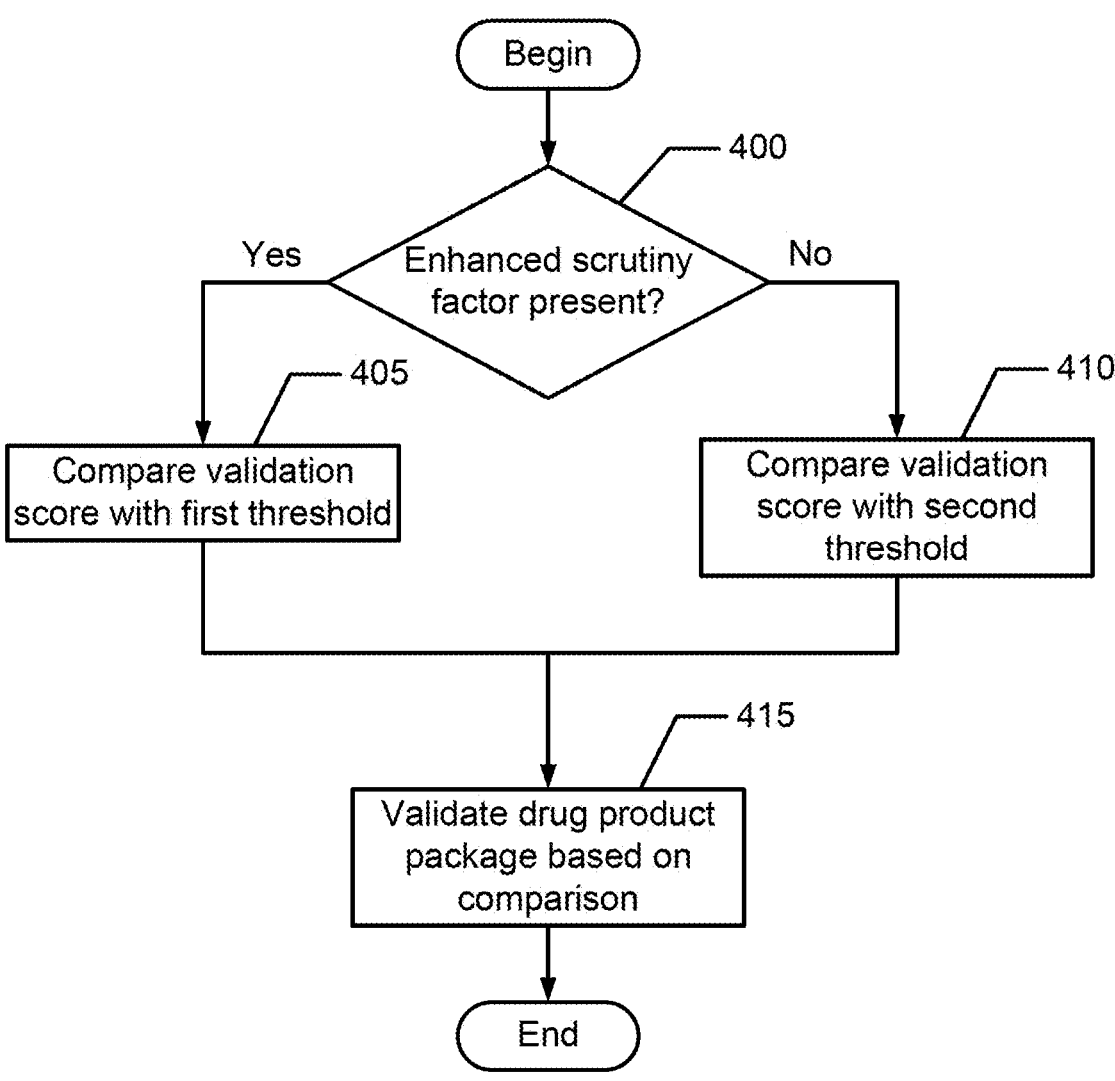
FIG. 4 is a flowchart that illustrates operations for validating a drug product package using tiered evaluation factors in accordance with further embodiments of the inventive concept.

FIG. 4 is a flowchart that illustrates operations for validating a drug product package using tiered evaluation factors in accordance with further embodiments of the inventive concept. Referring to FIG. 4, operations begin at block 400 where a determination is made whether one or more of the enhanced scrutiny factors has been found to be present in evaluating the drug product package. If one or more enhanced scrutiny factors is found to be present, then the magnitude of the validation may be compared with a first threshold at block 405. The drug product package may then be validated at block 415 if the magnitude of the validation score exceeds the first threshold. If none of the enhanced scrutiny factors are found to be present, then the operations continue at block 410 where the magnitude of the validation score is compared with a second threshold. The drug product package may then be validated at block 415 if the magnitude of the validation score exceeds the second threshold. In the embodiments of FIG. 4, the first threshold may be set higher than the second threshold so that if one or more enhanced scrutiny factors is found to be present, a higher validation score threshold may be established for the drug product package to be validated relative to a drug product package for which none of the enhanced scrutiny factors are implicated. Thus, when one or more of the enhanced scrutiny factors are present, the drug product package may be validated at block 415 when the magnitude of the validation score exceeds the first threshold. When none of the enhanced scrutiny factors are present, the drug product package may be validated at block 415 when the magnitude of the validation score exceeds the second threshold. The magnitude of the first threshold may be dynamic in that it's level may be based on a number of the enhanced scrutiny factors that are present and/or the particular ones of the enhanced scrutiny factors that are present. That is, in some embodiments, the enhanced scrutiny factors are not all considered of equal importance or concern such that the presence of certain enhanced scrutiny factors may justify setting a higher threshold that must be exceeded before validation. In other embodiments, the enhanced scrutiny factors may be divided into subsets such that the presence of one or more enhanced scrutiny factors from a first subset results in manual validation as described above with respect to block 220 of FIG. 2 while the presence one or more enhanced scrutiny factors from a second subset without any enhanced scrutiny factors from the first subset may allow the drug product package to be validated based on comparison of the validation score with a threshold, e.g., the first threshold described above with respect to blocks 405 and 415.

Figure 5:
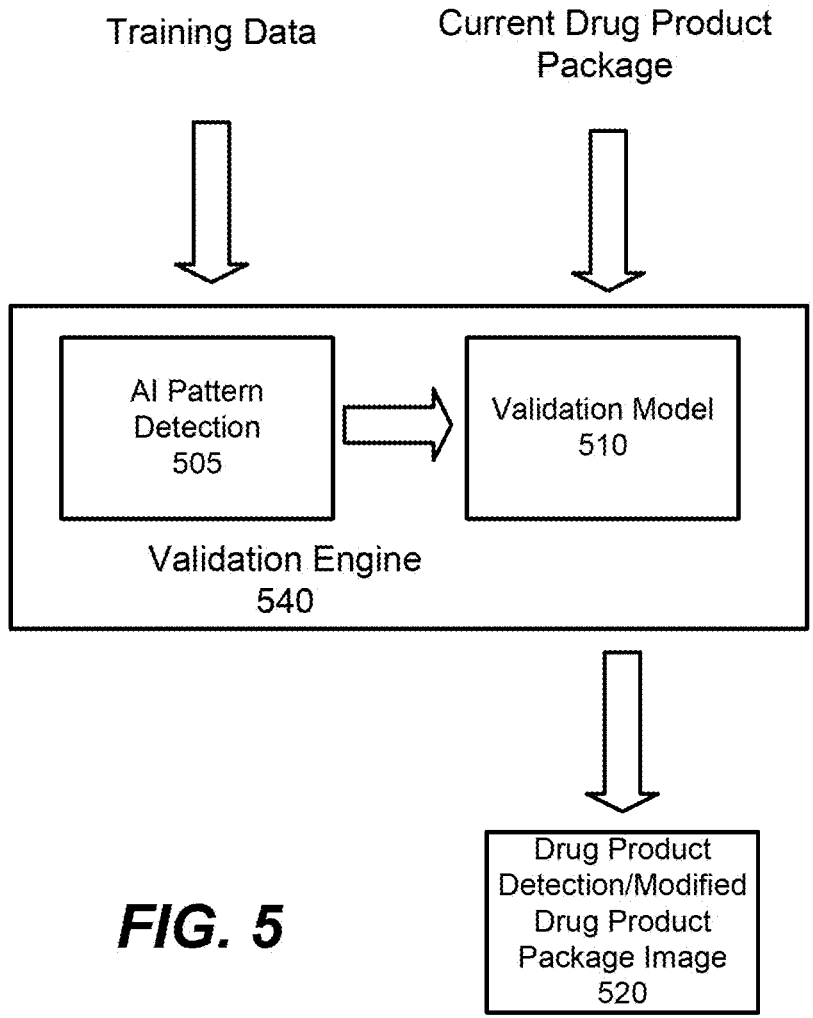
FIG. 5 is a block diagram that illustrates the drug product package validation system in accordance with further embodiments of the inventive concept.

As described above, the drug product package validation system, according to embodiments of the inventive concept, may use AI to facilitate the validation of the drug product packages including detection of the one or more drug products contained therein. In some embodiments, the drug product package validation system may include one or more AI systems to generate modified images of drug product packages with labeling content removed from one or more surfaces thereof, to detect in a drug product package image individual ones of one or more drug products contained in the drug product package, and/or to identify these drug products that have been detected in the drug product package image. FIG. 5 is a block diagram that illustrates a drug product package validation system including one or more AI systems or engines in accordance with further embodiments of the inventive concept. As shown in FIG. 5, the drug product validation system includes a validation engine 540, which may be a machine learning engine comprising an AI pattern detection module 505 and a validation model 510. The AI pattern detection module 505 is configured to receive training data. The training data may comprise one or more images of a drug product package that each contain one or more drug products therein. The drug product package may include labeling content on a surface thereof, which may include, but is not limited to, commercial marketing information, patient identification information and/or personal healthcare information (PHI). The commercial marketing information may include, for example, a logo and/or a business name. The patient identification information may include, for example, a patient name, a patient phone number, a patient address, and/or a patient identification number. The personal health care information may include, for example, names of the one or more drug products contained in the drug product package, a time of administration for each of the one or more drug products, one or more barcodes associated with the one or more drug products, a prescription order, a patient account, an identification number, and/or other information. The training data may include names for the one or more drug products in the drug product package. Different drug product packaging systems may differ from one another with respect to characteristics that can affect the detection/identification of one or more drug products in a drug product package and/or the removal of labeling content from a drug product package. Thus, the training data may include information related to characteristics of the one or more images that are associated with the drug product packaging system used to package the drug product. These characteristics may comprise one or more image capture light source characteristics, one or more image capture surface characteristics, one or more packaging material characteristics, and/or one or more camera characteristics. The one or more light source characteristics may comprise, for example, strength of an image capture light source, intensity of the image capture light source, and/or location of the image capture light source. The one or more image capture surface characteristics may comprise background location and/or background color. The one or more packaging material characteristics may comprise packaging material transparency, packaging material shadow, labeling color, packaging material color, and/or packaging material hot spot. The one or more camera characteristics comprise camera number, camera position, camera resolution, and/or camera image type. The training data may further include reference drug product package images including information identifying the drug product package characteristics and/or the contents contained therein. These known reference packages may serve as a baseline for the AI pattern detection module 505 to learn and the validation model 510 to recognize deviations in the characteristics of different drug product packaging systems relative to known reference images. Thus, the AI pattern detection module 505 may learn associations between content on the surfaces of drug product packages and content that is extraneous, associations between drug product images and drug product names, and/or associations between drug product debris and drug product names. The AI pattern detection module 505 may then generate a validation model 510 based on these learned associations, which can be used to facilitate validation of a drug product package by detecting drug products contained within the package and/or generating modified drug product package images in which extraneous surface content is removed. The identities of the drug products contained within the drug product package and/or modified drug product package images 520 may be output for use in drug product package validation.

Figures 6, 7, 8:
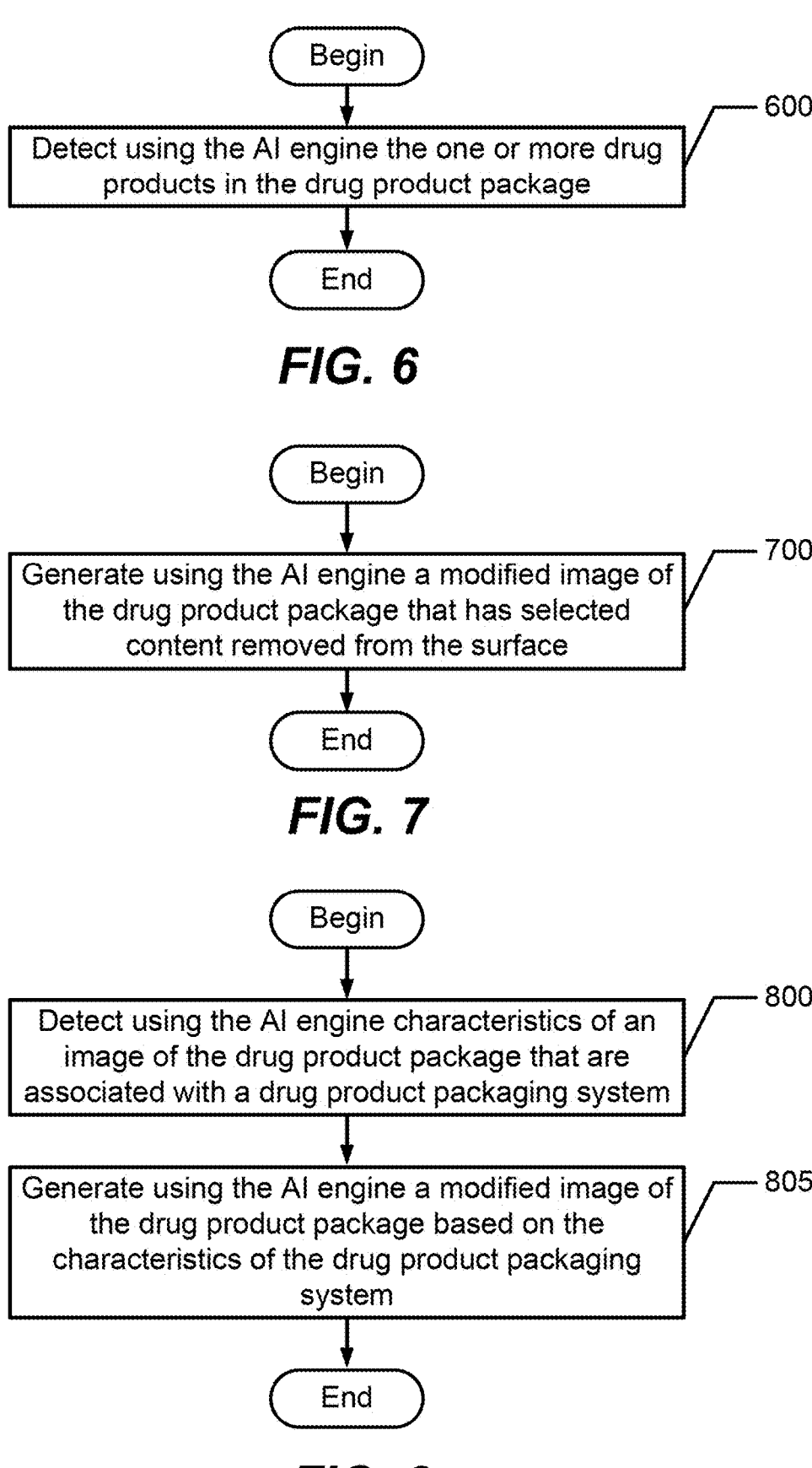
FIGS. 6-8 are flowcharts that illustrate operations for validating a drug product package using tiered evaluation factors in accordance with further embodiments of the inventive concept.

FIGS. 6-8 are flowcharts that illustrate operations for validating a drug product package using tiered evaluation factors in accordance with further embodiments of the inventive concept. Referring now to FIG. 6, operations begin at block 600 where the AI engine, e.g., the validation engine 540 of FIG. 5, is used to detect one or more drug products in the drug product package. This information can be used in evaluating whether one or more of the drug product packages implicate one or more of the drug product evaluation factors as described above with respect to FIG. 2, block 205. Referring now to FIG. 7, the AI engine, e.g., the validation engine 540 of FIG. 5, is used to generate a modified image of the drug product package that has selected content removed from the surface at block 700. The removal of extraneous content may assist the drug product validation system in evaluating the one or more drug products contained within the drug product package. Referring now to FIG. 8, the AI engine, e.g., the validation engine 540 of FIG. 5, is used to detect the characteristics of an image of the drug product package that are associated with the drug product packaging system at block 800. A modified image of the drug product package based on the characteristics of the drug product packaging system may be generated at block 805. According to the embodiments of FIG. 8, the drug product package validation system may take into account and compensate for differences between drug product packaging systems when evaluating the one or more drug products contained within the drug product packages during the validation process.

Figure 9:
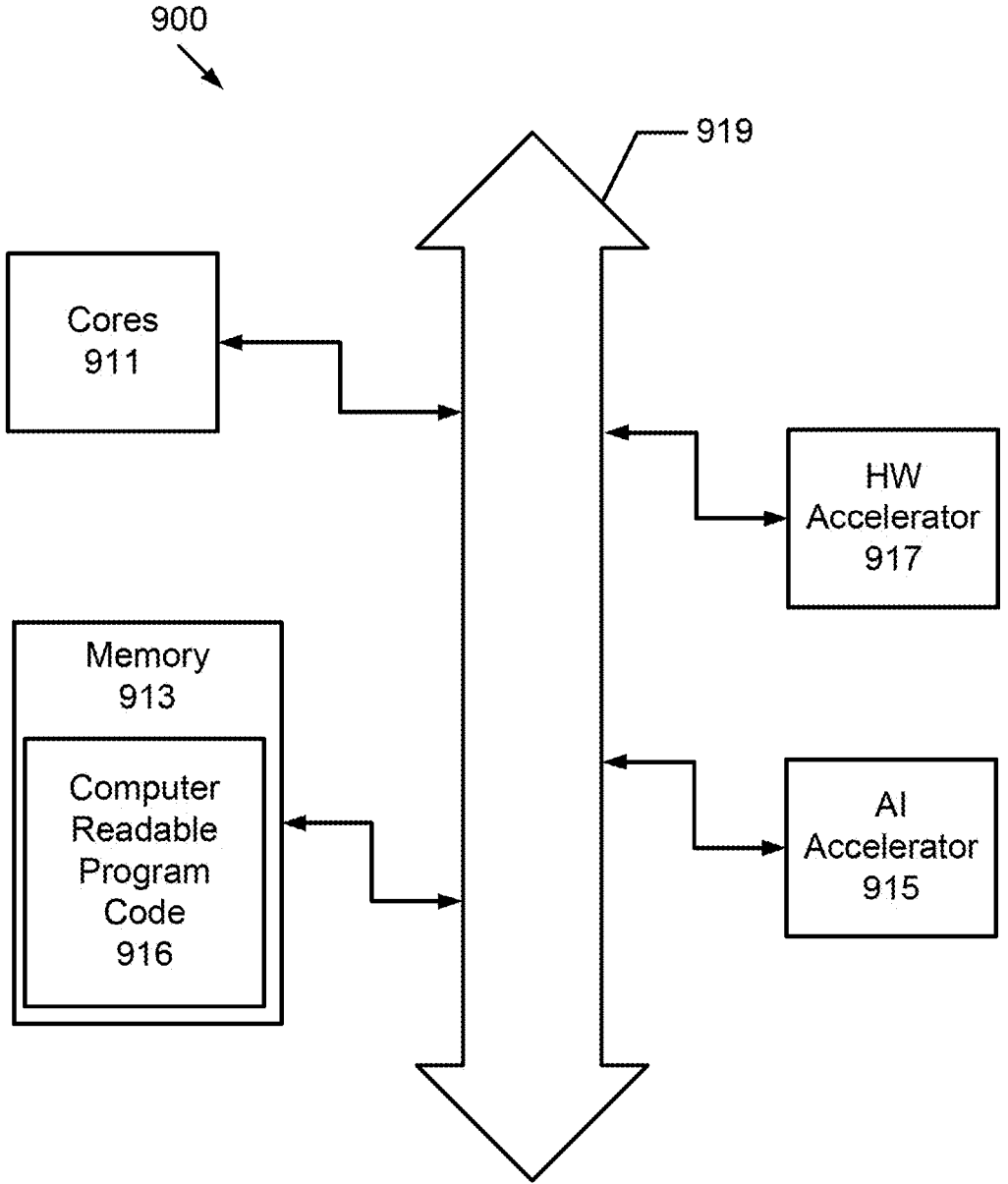
FIG. 9 is a data processing system that may be used to implement a drug product package validation system for validating a drug product using tiered evaluation factors in accordance with some embodiments of the inventive concept.

FIG. 9 is a block diagram of a data processing system 900 that may be used to implement the validation system server 155 of FIG. 1 and/or validation engines 340 and 540 of FIGS. 3 and 5 in accordance with some embodiments of the inventive concept. As shown in FIG. 9, the data processing system may include at least one core 911, a memory 913, an artificial intelligence (AI) accelerator 915, and a hardware (HW) accelerator 917. The at least one core 911, the memory 913, the AI accelerator 915, and the HW accelerator 917 may communicate with each other through a bus 919.

The at least one core 911 may be configured to execute computer program instructions. For example, the at least one core 911 may execute an operating system and/or applications represented by the computer readable program code 916 stored in the memory 913. In some embodiments, the at least one core 911 may be configured to instruct the AI accelerator 915 and/or the HW accelerator 917 to perform operations by executing the instructions and obtain results of the operations from the AI accelerator 915 and/or the HW accelerator 917. In some embodiments, the at least one core 911 may be an Application Specific Instruction-Set Processor (ASIP) customized for specific purposes and support a dedicated instruction set.

The memory 913 may have an arbitrary structure configured to store data. For example, the memory 913 may include a volatile memory device, such as dynamic random-access memory (DRAM) and static RAM (SRAM), or include a non-volatile memory device, such as flash memory and resistive RAM (RRAM). The at least one core 911, the AI accelerator 915, and the HW accelerator 917 may store data in the memory 913 or read data from the memory 913 through the bus 919.

The AI accelerator 915 may refer to hardware designed for AI applications. In some embodiments, the AI accelerator 915 may include a machine learning engine configured to facilitate validation of a drug product package using tiered evaluation factors. The AI accelerator 915 may generate output data by processing input data provided from the at least one core 915 and/or the HW accelerator 917 and provide the output data to the at least one core 911 and/or the HW accelerator 917. In some embodiments, the AI accelerator 915 may be programmable and be programmed by the at least one core 911 and/or the HW accelerator 917. The HW accelerator 917 may include hardware designed to perform specific operations at high speed. The HW accelerator 917 may be programmable and be programmed by the at least one core 911.

Figure 10:
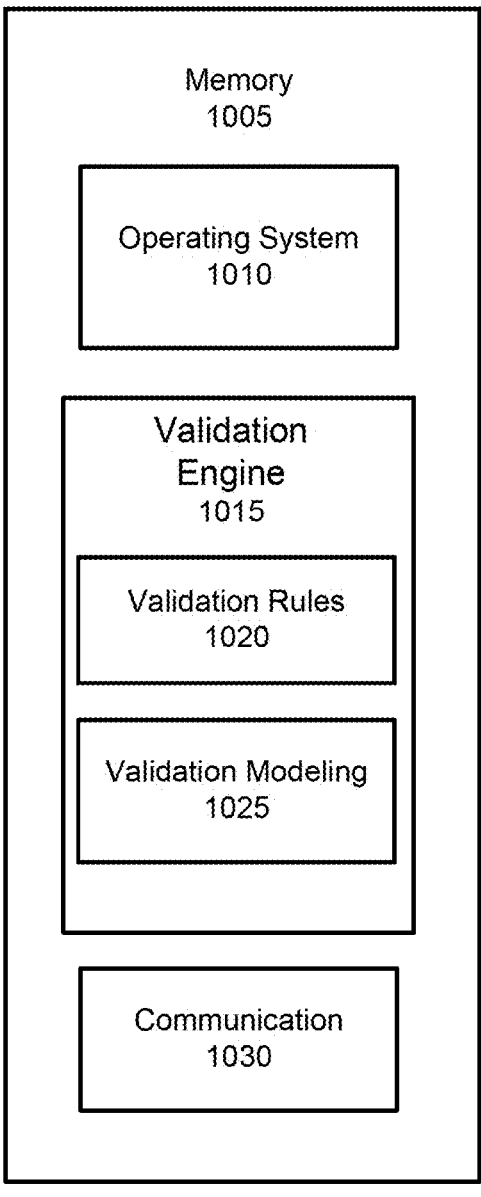
FIG. 10 is a block diagram that illustrates a software/hardware architecture for use in in a drug product package validation system for validating a drug product using tiered evaluation factors in accordance with some embodiments of the inventive concept.

FIG. 10 illustrates a memory 1005 that may be used in embodiments of data processing systems, such as the validation system server 155 of FIG. 1 and/or validation engines 340 and 540 of FIGS. 3 and 5, and the data processing system 900 of FIG. 9, respectively, to facilitate validating a drug product package using tiered evaluation factors. The memory 1005 is representative of the one or more memory devices containing the software and data used for facilitating operations of the validation system server 155 and package validation engine module 160 as described herein. The memory 1005 may include, but is not limited to, the following types of devices: cache, ROM, PROM, EPROM, EEPROM, flash, SRAM, and DRAM. As shown in FIG. 10, the memory 1005 may contain three or more categories of software and/or data: an operating system 1010, a validation engine 1015, and a communication module 1030. In particular, the operating system 1010 may manage the data processing system's software and/or hardware resources and may coordinate execution of programs by the processor.

The validation engine 1015 comprises a validation rules module 1020 and a validation modeling module 1025. The validation rules module may be configured to perform one or more of the operations described above with respect to FIG. 2 and the validation engine 340 of FIG. 3. The validation modeling module 1025 may be configured to perform one or more of the operations described above with respect to FIGS. 2 and 6-8 and the validation engine 540 of FIG. 5. The communication module 1030 may be configured to facilitate communication between the validation system server 155 of FIG. 1 and the packaging management system 110 and packaging system server 120 of FIG. 1.

Although FIGS. 9-10 illustrate hardware/software architectures that may be used in data processing systems, such as the validation system server 155 of FIG. 1 and the data processing system 900 of FIG. 9, respectively, in accordance with some embodiments of the inventive concept, it will be understood that embodiments of the present invention are not limited to such a configuration but are intended to encompass any configuration capable of carrying out operations described herein.

Computer program code for carrying out operations of data processing systems discussed above with respect to FIGS. 1-9 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the validation system server 155 of FIG. 1 and the data processing system 900 of FIG. 9 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus described with respect to FIGS. 1-10 may be used to facilitate validation of drug product packages using tired evaluation factors according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 1005 when coupled to a processor includes computer readable program code that, when executed by the processor, causes the processor to perform operations including one or more of the operations described herein with respect to FIGS. 1-8.

As described above, embodiments of the inventive concept may provide drug product package validation system that may provide a packaging entity, such as a pharmacy, medical center, or the like, flexibility in creating a tiered set of evaluation factors for validating a drug product package. The tiered evaluation factors may specify one or more factors as being enhanced scrutiny factors the presence of which may trigger a manual review of a drug product package or an increased validation score magnitude before the drug product package is considered to be validated. These evaluation factors, including the enhanced scrutiny factors, may be defined or assigned on a per order basis and/or may apply to multiple packaging orders. This flexibility may allow a packaging entity to place increased emphasis on certain evaluation factors to reduce patient risk as well as the risk to the packager of, for example, improperly packaging and ultimately wasting a high-cost drug product.

FURTHER DEFINITIONS AND EMBODIMENTS

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random-access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises," "comprising," "include", "including", "includes", "have", "has", "having", or variants thereof when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

It will also be understood that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method comprising:
receiving a drug product package containing one or more drug products therein;
evaluating the one or more drug products contained in the drug product package based on a plurality of drug product evaluation factors, the plurality of drug product evaluation factors including an enhanced scrutiny factor;
assigning a validation score to the drug product package based on evaluating the one or more drug products contained in the drug product package, a magnitude of the validation score being greater with decreasing patient risk; and
validating the drug product package;
wherein validating the drug product package comprises:
generating, using an artificial intelligence engine, a modified image of the drug product package;
detecting, using the artificial intelligence engine, the one or more drug products contained in the drug product package based on the modified image; and
validating the drug product package based on the modified image and a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold.

2. The method of claim 1, wherein the drug product package is part of a fulfillment of a packaging order; and
wherein the method further comprises:
defining the enhanced scrutiny factor for the packaging order.

3. The method of claim 1, wherein the drug product package is part of a fulfillment of a packaging order;
wherein the method further comprises:
defining the first threshold and the second threshold for the packaging order.

4. The method of claim 1, wherein the plurality of drug product evaluation factors include a plurality of enhanced scrutiny factors, the plurality of enhanced scrutiny factors comprising a first subset of enhanced scrutiny factors and a second subset of enhanced scrutiny factors.

5. The method of claim 4, wherein validating the drug product package comprises:

validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors; and validating the drug product package based on a second comparison of the magnitude of the validation score with the second threshold responsive to an absence of any of the plurality of enhanced scrutiny factors.

6. The method of claim 5, wherein validating the drug product package further comprises:

identifying the drug product package as requiring manual validation responsive to the presence of the at least one enhanced scrutiny factor of the second subset of enhanced scrutiny factors.

7. The method of claim 4, wherein the plurality of enhanced scrutiny factors comprises one or more of:

an age of a patient to whom the one or more drug products is prescribed;

a gender of the patient to whom the one or more drug products is prescribed;

a pharmacogenomic profile of the patient to whom the one or more drug products is prescribed;

a financial cost of the one or more drug products;

an interaction between the one or more drug products;

a side effect of the one or more drug products;

a propensity of the one or more drug products to create debris in the drug product package;

packaging order history information for the patient to whom the one or more drug products is prescribed;

recall information for the one or more drug products;

a potential for exceeding a safe dosing for the one or more drug products; and an indication that the one or more drug products includes a substituted drug product that differs from a packaging order.

8. The method of claim 1, wherein generating, using the artificial intelligence engine, the modified image of the drug product package comprises:

generating, using the artificial intelligence engine, the modified image of the drug product package that has selected content removed from a surface thereof.

9. The method of claim 1, wherein generating, using the artificial intelligence engine, the modified image of the drug product package comprises:

detecting, using the artificial intelligence engine, characteristics of an image of the drug product package that are associated with a drug product packaging system; and generating, using the artificial intelligence engine, the modified image of the drug product package based on characteristics of the drug product packaging system.

10. A system, comprising:

a processor; and a memory coupled to the processor and comprising computer readable program code embodied in the memory that is executable by the processor to perform operations comprising:

receiving a drug product package containing one or more drug products therein;

evaluating the one or more drug products contained in the drug product package based on a plurality of drug product evaluation factors, the plurality of drug product evaluation factors including an enhanced scrutiny factor;

assigning a validation score to the drug product package based on evaluating the one or more drug products contained in the drug product package, a magnitude of the validation score being greater with decreasing patient risk; and validating the drug product package;

wherein validating the drug product package comprises:

generating, using an artificial intelligence engine, a modified image of the drug product package;

detecting, using the artificial intelligence engine, the one or more drug products contained in the drug product package based on the modified image; and validating the drug product package based on the modified image and a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold.

11. The system of claim 10, wherein the plurality of drug product evaluation factors include a plurality of enhanced scrutiny factors, the plurality of enhanced scrutiny factors comprising a first subset of enhanced scrutiny factors and a second subset of enhanced scrutiny factors.

12. The system of claim 11, wherein validating the drug product package comprises:

validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors; and validating the drug product package based on a second comparison of the magnitude of the validation score with the second threshold responsive to an absence of any of the plurality of enhanced scrutiny factors.

13. The system of claim 12, wherein validating the drug product package further comprises:

identifying the drug product package as requiring manual validation responsive to the presence of the at least one enhanced scrutiny factor of the second subset of enhanced scrutiny factors.

14. The system of claim 11, wherein the plurality of enhanced scrutiny factors comprises one or more of:

an age of a patient to whom the one or more drug products is prescribed;

a gender of the patient to whom the one or more drug products is prescribed;

a pharmacogenomic profile of the patient to whom the one or more drug products is prescribed;

a financial cost of the one or more drug products;

an interaction between the one or more drug products;

a side effect of the one or more drug products;

a propensity of the one or more drug products to create debris in the drug product package;

packaging order history information for the patient to whom the one or more drug products is prescribed;

recall information for the one or more drug products;

a potential for exceeding a safe dosing for the one or more drug products; and an indication that the one or more drug products includes a substituted drug product that differs from a packaging order.

15. A computer program product, comprising:

a non-transitory computer readable storage medium comprising computer readable program code embodied in the medium that is executable by a processor to perform operations comprising:

receiving a drug product package containing one or more drug products therein;

evaluating the one or more drug products contained in the drug product package based on a plurality of drug product evaluation factors, the plurality of drug product evaluation factors including an enhanced scrutiny factor;

assigning a validation score to the drug product package based on evaluating the one or more drug products contained in the drug product package, a magnitude of the validation score being greater with decreasing patient risk; and validating the drug product package;

wherein validating the drug product package comprises:

generating, using an artificial intelligence engine, a modified image of the drug product package;

detecting, using the artificial intelligence engine, the one or more drug products contained in the drug product package based on the modified image; and validating the drug product package based on the modified image and a first comparison of the magnitude of the validation score with a first threshold responsive to a presence of the enhanced scrutiny factor and a second comparison of the magnitude of the validation score with a second threshold responsive to an absence of the enhanced scrutiny factor, the first threshold being greater than the second threshold.

16. The computer program product of claim 15, wherein the plurality of drug product evaluation factors include a plurality of enhanced scrutiny factors, the plurality of enhanced scrutiny factors comprising a first subset of enhanced scrutiny factors and a second subset of enhanced scrutiny factors.

17. The computer program product of claim 16, wherein validating the drug product package comprises:

validating the drug product package based on the first comparison of the magnitude of the validation score with the first threshold responsive to a presence of at least one enhanced scrutiny factor of the first subset of enhanced scrutiny factors and absent a presence of at least one enhanced scrutiny factor of the second subset of enhanced scrutiny factors;

validating the drug product package based on a second comparison of the magnitude of the validation score with the second threshold responsive to an absence of any of the plurality of enhanced scrutiny factors; and identifying the drug product package as requiring manual validation responsive to the presence of the at least one enhanced scrutiny factor of the second subset of enhanced scrutiny factors.

18. The system of claim 10, wherein generating, using the artificial intelligence engine, the modified image of the drug product package comprises:

generating, using the artificial intelligence engine, the modified image of the drug product package that has selected content removed from a surface thereof.

19. The system of claim 10, wherein generating, using the artificial intelligence engine, the modified image of the drug product package comprises:

detecting, using the artificial intelligence engine, characteristics of an image of the drug product package that are associated with a drug product packaging system; and generating, using the artificial intelligence engine, the modified image of the drug product package based on characteristics of the drug product packaging system.

20. The computer program product of claim 16, wherein the plurality of enhanced scrutiny factors comprises one or more of:

an age of a patient to whom the one or more drug products is prescribed;

a gender of the patient to whom the one or more drug products is prescribed;

a pharmacogenomic profile of the patient to whom the one or more drug products is prescribed;

a financial cost of the one or more drug products;

an interaction between the one or more drug products;

a side effect of the one or more drug products;

a propensity of the one or more drug products to create debris in the drug product package;

packaging order history information for the patient to whom the one or more drug products is prescribed;

recall information for the one or more drug products;

a potential for exceeding a safe dosing for the one or more drug products; and an indication that the one or more drug products includes a substituted drug product that differs from a packaging order.

* * * * *